United States Patent
Leinweber et al.

(10) Patent No.: US 12,037,537 B2
(45) Date of Patent: Jul. 16, 2024

(54) METHOD OF AND A COMPOSITION FOR CONTROLLING GAS HYDRATE BLOCKAGE THROUGH THE ADDITION OF A SYNERGISTICALLY ACTING BLEND WITH ALKOXYLATES OF FATTY ALCOHOLS, FATTY AMINES AND FATTY ACIDS

(71) Applicant: Clariant International, Ltd., Muttenz (CH)

(72) Inventors: Dirk Leinweber, Kelkheim (DE); Zachary Thomas Ward, Spring, TX (US); Felix Hoevelmann, Mühldorf (DE); Jonathan James Wylde, The Woodlands, TX (US)

(73) Assignee: Clariant International Ltd, Muttenz (CH)

( * ) Notice: Subject to any disclaimer, the term of this patent is extended or adjusted under 35 U.S.C. 154(b) by 0 days.

(21) Appl. No.: 17/099,494

(22) Filed: Nov. 16, 2020

(65) Prior Publication Data

US 2021/0179921 A1    Jun. 17, 2021

Related U.S. Application Data

(60) Provisional application No. 62/946,679, filed on Dec. 11, 2019.

(51) Int. Cl.
| | |
|---|---|
| *E21B 43/16* | (2006.01) |
| *C07D 207/404* | (2006.01) |
| *C09K 8/52* | (2006.01) |
| *C10L 1/222* | (2006.01) |
| *C10L 3/10* | (2006.01) |

(52) U.S. Cl.
CPC ............ *C09K 8/52* (2013.01); *C07D 207/404* (2013.01); *C10L 1/2222* (2013.01); *C10L 3/107* (2013.01); *C09K 2208/22* (2013.01)

(58) Field of Classification Search
None
See application file for complete search history.

(56) References Cited

U.S. PATENT DOCUMENTS

| | | | |
|---|---|---|---|
| 4,832,871 A * | 5/1989 | Bade | ................. C07C 233/89 |
| | | | 516/900 |
| 4,915,176 A | 4/1990 | Sugier | |
| 4,973,775 A | 11/1990 | Sugier | |
| 5,244,878 A | 9/1993 | Sugier | |
| 5,460,728 A | 10/1995 | Klomp | |
| 5,648,575 A | 7/1997 | Klomp | |
| 5,879,561 A | 3/1999 | Klomp | |
| 6,015,929 A | 1/2000 | Rabeony | |
| 6,369,004 B1 * | 4/2002 | Klug | ...................... C08F 8/32 |
| | | | 210/698 |
| 6,596,911 B2 | 7/2003 | Przybylinski | |
| 7,381,689 B2 | 6/2008 | Panchalingam | |
| 9,765,254 B2 | 9/2017 | Lucente-Schultz | |
| 10,870,789 B2 | 12/2020 | Pou | |
| 2004/0163306 A1 | 8/2004 | Dahlmann | |
| 2004/0167040 A1 | 8/2004 | Dahlmann | |
| 2005/0081432 A1 * | 4/2005 | Panchalingam | ......... C10L 3/108 |
| | | | 44/419 |
| 2005/0101495 A1 | 5/2005 | Dahlmann | |
| 2006/0237691 A1 | 10/2006 | Meier | |
| 2007/0079963 A1 | 4/2007 | Yang | |
| 2009/0042749 A1 | 2/2009 | Meier | |
| 2009/0173663 A1 | 7/2009 | Leinweber | |
| 2010/0087339 A1 | 4/2010 | Acosta | |
| 2010/0116642 A1 | 5/2010 | Krull | |
| 2014/0021262 A1 * | 1/2014 | Matsumura | .......... H05K 1/0283 |
| | | | 235/488 |
| 2014/0091262 A1 | 4/2014 | Webber | |
| 2016/0122619 A1 | 5/2016 | Lucente-Schultz | |
| 2016/0186039 A1 | 6/2016 | Owsik | |
| 2017/0305838 A1 | 10/2017 | Appel | |
| 2018/0030340 A1 * | 2/2018 | McCabe | ................. C09K 8/528 |
| 2018/0333339 A1 | 11/2018 | Hamersky | |
| 2018/0346790 A1 | 12/2018 | Pou | |
| 2018/0346791 A1 | 12/2018 | Bartels | |

FOREIGN PATENT DOCUMENTS

| | | |
|---|---|---|
| CN | 101906293 | 12/2010 |
| CN | 105733539 | 7/2016 |
| EP | 0651049 | 5/1995 |
| GB | 2349889 | 11/2000 |

(Continued)

OTHER PUBLICATIONS

International Preliminary Report on Patentability for App. No. PCT/EP2020/084719, dated May 17, 2022, 8 pages.
International Search Report for App. No. PCT/EP2020/084718, dated Mar. 4, 2021, 2 pages.
International Search Report for App. No. PCT/EP2020/084719, dated Mar. 4, 2021, 3 pages.
International Search Report for App. No. PCT/EP2020/084722, dated Mar. 4, 2021, 3 pages.
International Search Report for App. No. PCT/EP2020/084726, dated Mar. 4, 2021, 3 pages.
International Search Report and Written Opinion for App. No. PCT/EP2020/084717, dated Mar. 3, 2021, 14 pages.
International Search Report and Written Opinion for App. No. PCT/EP2020/084721, dated Mar. 4, 2021, 16 pages.
International Search Report and Written Opinion for App. No. PCT/EP2020/084724, dated Mar. 4, 2021, 16 pages.

(Continued)

*Primary Examiner* — Charles R Nold

(57) ABSTRACT

Provided herein is a method for inhibiting gas hydrate formation in a system containing hydrocarbons and water. The method includes contacting the system with a gas hydrate inhibitor composition including an amidoamine of a fatty acid, optionally in the form of a cationic ammonium compound, and a nonionic surfactant selected from alkoxylated $C_8$-$C_{18}$ fatty alcohols, alkoxylated $C_8$-$C_{18}$ fatty amines, alkoxylated $C_8$-$C_{18}$ fatty acids and alkoxylated $C_8$-$C_{18}$ fatty acid amides.

19 Claims, No Drawings

(56) References Cited

FOREIGN PATENT DOCUMENTS

| GB | 2542656 A | * | 3/2017 | ............. C09K 8/035 |
|---|---|---|---|---|
| WO | 2002066785 | | 8/2002 | |
| WO | 2005042675 | | 5/2005 | |
| WO | 2006072083 | | 7/2006 | |
| WO | 2012082815 | | 6/2012 | |
| WO | 2012102916 | | 8/2012 | |
| WO | 2013089802 | | 6/2013 | |
| WO | 2016069987 | | 5/2016 | |
| WO | 2017089724 | | 6/2017 | |
| WO | 2017184115 | | 10/2017 | |
| WO | 2017223306 | | 12/2017 | |
| WO | 2018115186 | | 6/2018 | |
| WO | 2019015828 | | 1/2019 | |

OTHER PUBLICATIONS

International Search Report for App. No. PCT/EP2019/074182 dated Dec. 6, 2019, 4 pages.
Khan (M. S. Khan et al., Tetramethyl ammonium chloride as dual functional inhibitor for methane and carbon dioxide hydrates, Fuels 2019, 236, 251-263).
M. Sun, et al., J. Colloid Interf. Sci., 402 (2013), pp. 312-319.
Machine translation of CN101906293, Aug. 12, 2010, 24 pages.
Product data sheet for TetraMethylAmmonium Chloride, downloaded on Jan. 29, 2022, 8 pages.
Whitmore et al., "Basically Substituted Aliphatic Nitriles and their Catalytic Reduction to Amines", Jornal of American Chemical Society, vol. 66, May 1944, pp. 725-731.

* cited by examiner

METHOD OF AND A COMPOSITION FOR CONTROLLING GAS HYDRATE BLOCKAGE THROUGH THE ADDITION OF A SYNERGISTICALLY ACTING BLEND WITH ALKOXYLATES OF FATTY ALCOHOLS, FATTY AMINES AND FATTY ACIDS

CROSS REFERENCE TO RELATED APPLICATION

This application claims priority to U.S. Provisional Patent Application No. 62/946,679, filed Dec. 11, 2019, the entirety of which is hereby incorporated herein by reference.

This invention relates to the prevention of gas hydrate blockage in oil and natural gas pipelines containing low-boiling point hydrocarbons and water. More specifically, the invention relates to a method of controlling gas hydrate blockage through the addition of a synergistically acting blend of chemical compositions.

When hydrocarbon gas molecules dissolve in water, the hydrogen-bonded network of water molecules encapsulates the gas molecules to form a cage-like structure or hydrate. Higher pressures and lower temperatures foster the formation of these structures. These hydrates grow by encapsulating more and more gaseous molecules to form a crystalline mass. The crystalline mass agglomerates to form a larger mass that can result in a plugged transmission line. The hydrocarbon gases that form the majority of the hydrates include methane, ethane, propane, n-butane, iso-butane, n-pentane, iso-pentane, and combinations of these gases.

Thermodynamic hydrate inhibitors, such as methanol or one of the glycols, have traditionally been used to prevent these hydrate formations. These thermodynamic inhibitors are effective at 5-50% (or higher) based on the amount of water. As oil companies are exploring new production in deep waters, the total gas/oil/water productions are also increasing. The use of these thermodynamic inhibitors is not viable in these applications due to logistical constraints of supplying and pumping such vast quantities of fluids to often remote locations.

Kinetic hydrate inhibitors have been identified to prevent these hydrate formations so that the fluids can be pumped out before a catastrophic hydrate formation occurs. The kinetic inhibitors prevent or delay hydrate crystal nucleation and disrupt crystal growth. These kinetic hydrate inhibitors contain moieties similar to gas molecules previously mentioned. It is suspected that these kinetic inhibitors prevent hydrate crystal growth by becoming incorporated into the growing hydrate crystals, thereby disrupting further hydrate crystal growth. The growing hydrate crystals complete a cage by combining with the partial hydrate-like cages around the kinetic hydrate inhibitor moieties containing gas-like groups. These inhibitors are effective with or without the presence of a liquid hydrocarbon phase, but they are typically less effective in preventing the hydrate formation as the production pressure increases. Examples of kinetic hydrate inhibitors include poly(N-methylacrylamide), poly(N,N-dimethylacrylamide), poly(N-ethylacrylamide), poly(N,N-diethylacrylamide), poly(N-methyl-N-vinylacetamide), poly(2-ethyloxazoline), poly(N-vinylpyrrolidone), and poly(N-vinylcaprolactam).

Unlike the kinetic hydrate inhibitors, anti-agglomerates are effective only in the presence of an oil phase. Anti-agglomerates do not inhibit the formation of gas hydrates to the same level as kinetic inhibitors, rather their primary activity is in preventing the agglomeration of hydrate crystals. The oil phase provides a transport medium for the hydrates which are referred to as hydrate slurries so that the overall viscosity of the medium is kept low and can be transported along the pipeline. As such, the hydrate crystals formed in the water-droplets are prevented from agglomerating into a larger crystalline mass.

Examples of several chemicals acting as anti-agglomerates have been reported in U.S. Pat. Nos. 5,460,728; 5,648,575; 5,879,561; and 6,596,911. These patents teach the use of quaternary ammonium salts having at least three alkyl groups with four or five carbon atoms and a long chain hydrocarbon group containing 8-20 atoms. Exemplary compositions include tributylhexadecylphosphonium bromide and tributylhexadecylammonium bromide.

U.S. Pat. No. 5,460,728 teaches the use of alkylated ammonium, phosphonium or sulfonium compounds having three or four alkyl groups in their molecule, at least three of which are independently chosen from the group of normal or branched alkyls having four to six carbon atoms.

U.S. Pat. No. 5,648,575 teaches very similar compositions having three or four organic groups in their molecule, at least three of which have at least four carbon atoms, i.e., two normal or branched alkyl groups having at least four carbon atoms and with a further organic moiety containing a chain of at least four carbon atoms.

U.S. Pat. No. 5,879,561 teaches the use of alkylated ammonium or phosphonium compounds having four alkyl groups, two of which are independently normal or branched alkyls having four or five carbon atoms and two more of which independently represent organic moieties having at least eight carbon atoms.

U.S. Pat. No. 6,369,004 B1 teaches the kinetic inhibition of gas hydrate formation using polymers based on reacting maleic anhydride with one or more amines. These polymers can also be used together with various other substances, called synergists, including tetrabutylammonium salts, tetrapentylammonium salts, tributylamine oxide, tripentylamine oxide, zwitterionic compounds having at least one butyl or pentyl group on the quaternary ammonium nitrogen atom, such as $Bu_3N^+$—$CH_2$—$COO^-$. However, kinetic inhibitors are not effective as the pipeline pressure increases.

U.S. Pat. No. 6,015,929 teaches the use of specific zwitterionic compounds such as $R(CH_3)_2N^+$—$(CH_2)_4$—$SO_3^-$ as anti-agglomerates. The synthesis of this product involves the use of butyl sulfone.

U.S. Pat. No. 7,381,689 teaches a method and an amide composition used therein for inhibiting, retarding, mitigating, reducing, controlling and/or delaying formation of hydrocarbon hydrates or agglomerates of hydrates. The method may be applied to prevent or reduce or mitigate plugging of conduits, pipes, transfer lines, valves, and other places or equipment where hydrocarbon hydrate solids may form under the conditions. At least one amide compound is added into the process stream, where the compound may be mixed with another compound selected from amino alcohols, esters, quaternary ammonium, phosphonium or sulfonium salts, betaines, amine oxides, other amides, simple amine salts, and combinations thereof.

However, there remains a need for hydrate inhibitor compounds that effectively prevent agglomeration of hydrates in oil and gas transportation and handling processes. It would be desirable to identify hydrate inhibitor compounds that are effective at lower dosages, higher pressures and/or lower temperatures such as those encountered in deep water production.

Surprisingly, it has been found that a gas hydrate inhibitor that comprises an amidoamine of a fatty acid, which optionally is in the form of a cationic ammonium compound, will be enhanced in its performance as a gas hydrate inhibitor when used together in a mixture with a synergistic surfactant which comprises a nonionic surfactant which is selected from alkoxylated $C_8$-$C_{18}$ fatty alcohols, alkoxylated $C_8$-$C_{18}$ fatty amines, alkoxylated $C_8$-$C_{18}$ fatty acids and alkoxylated $C_8$-$C_{18}$ fatty acid amides.

In a first embodiment, the instant invention provides a gas hydrate inhibitor composition, comprising
A) from 5 to 95 weight-% of a compound according to formula (1)

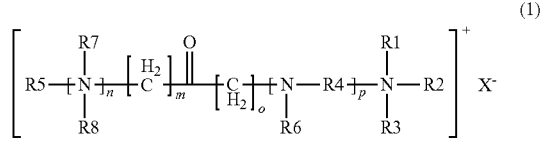
(1)

wherein
R1 is an alkyl group having from 1 to 5 carbon atoms;
R2 is hydrogen or an alkyl group having from 1 to 5 carbon atoms;
R3 is present or not as hydrogen and organic moieties having from 1 to 20 carbon atoms;
R4 is selected from —$(CH_2)_t$—, —$[CH_2$—$CHR^6)_t]$—, —$(CH_2$—$CHR^6O)_u$—$(CH_2)_t$— and combinations thereof;
R5 is an alkyl or alkenyl group having 4 to 22 carbon atoms;
R6 is hydrogen or an alkyl group having from 1 to 4 carbon atoms;
R7 is hydrogen or an alkyl group having from 1 to 4 carbon atoms;
R8 is present or not as hydrogen or organic moieties having from 1 to 20 carbon atoms;
t is 2, 3 or 4;
u is an integer between 0 and 100;
n is 0 or 1
m is 0 or 2
o is 0 or 2,
p is 0 or 1
$X^-$ is an anion,
and
B) from 5 to 95 weight-% of a compound that is a synergistic surfactant which is selected from alkoxylated $C_8$-$C_{18}$ fatty alcohols, alkoxylated $C_8$-$C_{18}$ fatty amines, alkoxylated $C_8$-$C_{18}$ fatty acids and alkoxylated $C_8$-$C_{18}$ fatty acid amides.

The synergistic surfactant is a surfactant that enhances the effect of the gas hydrate inhibitor. Whether or not there is a synergy between components A) and B) is determined by the reduced dose rate to prevent gas hydrate agglomeration over the dose rate required of each of the individual components. The reduction of dosage rate is at least 10-40 wt. %, preferably 20-40 wt. % and most preferably 25-40 wt. %.

In a preferred embodiment, the instant invention provides a gas hydrate inhibitor composition, wherein A) is a compound according to formula (1a)

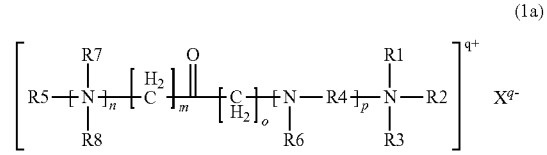
(1a)

wherein
R1 is an alkyl group having from 1 to 5 carbon atoms;
R2 is hydrogen or an alkyl group having from 1 to 5 carbon atoms;
R3 is present or not as hydrogen and organic moieties having from 1 to 20 carbon atoms;
R4 is selected from —$(CH_2)_t$—, —$[CH_2$—$CHR^6)_t]$—, —$(CH_2$—$CHR^6O)_u$—$(CH_2)_t$— and combinations thereof;
R5 is an alkyl or alkenyl group having 4 to 22 carbon atoms;
R6 is hydrogen or an alkyl group having from 1 to 4 carbon atoms;
R7 is hydrogen or an alkyl group having from 1 to 4 carbon atoms;
R8 is present or not as hydrogen or organic moieties having from 1 to 20 carbon atoms;
t is 2, 3 or 4;
u is an integer between 0 and 100;
n is 0 or 1
m is 0 or 2
o is 0 or 2,
p is 0 or 1,
q is an integer between 0 and 2
$X^-$ is an anion,
wherein q is 0 when R3 and R8 are absent; q is 1 when one of R3 and R8 is present and the other is absent; and q is 2 when R3 and R8 are both present.

In a preferred embodiment, the nonionic surfactant (B) is an alkoxylated $C_8$-$C_{18}$ fatty alcohol, an alkoxylated $C_8$-$C_{18}$ fatty amine, an alkoxylated $C_8$-$C_{18}$ fatty acid and/or an alkoxylated $C_8$-$C_{18}$ fatty acid amide of general formula (19):

(19)

wherein
$R^{11}$ is an alkyl or alkenyl group having 8 to 18 carbon atoms;
Y is —O—, —$N(R^{19})$—, —$C(=O)$—O— or —$C(=O)$—$N(R^{19})$—;
A is a $C_1$ to $C_4$ alkylene group;
$R^{12}$ is hydrogen, an alkyl group having from 1 to 5 carbon atoms, a benzyl group, or —$C(O)$—$R^{20}$
$R^{19}$ is hydrogen, an alkyl group having from 1 to 18 carbon atoms, an alkenyl group having 3 to 18 carbon atoms, or a group of formula -$(AO)_w$—$R^{12}$
$R^{20}$ is a $C_1$ to $C_5$-hydrocarbyl group; and
w is an integer between 1 and 25.

In a preferred embodiment, $R^{11}$ is an alkyl or alkenyl group having from 8 to 16 and more preferred from 10 to 14 carbon atoms, as for example from 8 to 14, or from 10 to 18, or from 10 to 16 carbon atoms. The alkyl or alkenyl group may be linear or branched. Preferably it is linear. Unsaturated alkenyl groups $R^{11}$ contain one or two double bonds. Examples for preferred alkyl or alkenyl groups are octyl, 2-ethyl hexyl, iso-nonyl, decyl, iso-undecyl, dodecyl, iso-tridecyl, tetradecyl, pentadecyl, hexadecyl, octadecyl, oleyl, and any mixtures thereof. In a preferred embodiment, $R^{11}$ comprises a mixture of different alkyl groups within the given chain lengths.

When Y is oxygen, the nonionic surfactant (B) is an alkoxylated fatty alcohol. When Y is $N(R^{19})$, the nonionic surfactant (B) is an alkoxylated fatty amine. When Y is a group of the formula —C(=O)—O—, the nonionic surfactant (B) is an alkoxylated fatty acid. When Y is a group of the formula —C(=O)—N($R^{19}$)—, the nonionic surfactant (B) is an alkoxyalted fatty acid amide. The terms "alkoxylated fatty alcohol", "alkoxylated fatty amine", "alkoxylated fatty acid" and "alkoxylated fatty acid amide" encompass the direct alkoxylation products of fatty alcohols, fatty acids and fatty amines wherein $R^{12}$ is hydrogen, as well as their end-capped derivatives as for example esters and ethers. In preferred esters $R^{12}$ is a group of formula —C(=O)—$R^{20}$. In preferred ethers $R^{12}$ is an alkyl group having from 1 to 5 carbon atoms or a benzyl group. In a preferred embodiment, $R^{12}$ is hydrogen. In a further preferred embodiment, $R^{12}$ is an alkyl group having from 1 to 4 carbon atoms. The alkyl group may be linear or branched. More preferably, it is linear. Examples for preferred residues $R^{12}$ are methyl, ethyl, propyl, n-butyl, sec-butyl and tert-butyl. Especially preferred is the methyl group.

The fatty alcohol, the fatty acid and the fatty amine being the basis for alkoxylation may be of synthetic origin or they may be derived from renewable sources. Preferred renewable sources for fatty alcohols, fatty acids and fatty amines are for example corn oil, canola oil, coconut oil, cottonseed oil, safflower oil, sesame oil, sunflower oil, palm oil, soybean oil, olive oil, hemp oil, wheat germ oil, palm kernel oil, tallow fat, hardened tallow fat and any combination thereof.

In a preferred embodiment, the fatty amine being the basis for alkoxylation is a primary amine. Upon alkoxylation of the primary amine, $R^{19}$ will be a group having the formula -(AO)$_w$—H. In a further preferred embodiment, the fatty amine being the basis for alkoxylation is a secondary amine wherein $R^{19}$ is an alkyl or alkenyl group. In a preferred embodiment, $R^{19}$ is an alkyl or alkenyl group having from 5 to 18 carbon atoms and more preferably having from 8 to 16 and especially preferred from 10 to 14 carbon atoms, as for example from 5 to 16, or from 5 to 14, or from 8 to 18, or from 8 to 14, from 10 to 18, or from 10 to 16 carbon atoms. The alkyl or alkenyl group may be linear or branched. Preferably it is linear. The alkyl group is saturated. The alkenyl group may have one or two double bonds. Examples for preferred alkyl or alkenyl residues are methyl, ethyl, octyl, 2-ethyl hexyl, iso-nonyl, decyl, iso-undecyl, dodecyl, iso-tridecyl, tetradecyl, pentadecyl, hexadecyl, octadecyl, oleyl, and any mixtures thereof. In a preferred embodiment, $R^{19}$ comprises a mixture of different alkyl or alkenyl groups within the given chain lengths. In this embodiment $R^{19}$ may be the same as $R^{11}$ or it may be different. In a preferred embodiment, $R^{11}$ and $R^{19}$ are the same.

In a further preferred embodiment, the alkyoxylated fatty acid amide is a tertiary amide wherein $R^{19}$ is an alkyl group having from 1 to 18 carbon atoms, an alkenyl group having from 3 to 18 carbon atoms, or a group of formula -(AO)$_w$—$R^{12}$. More preferably, $R^{19}$ is an alkyl group having 1 to 5 carbon atoms as for example a methyl, ethyl, propyl or butyl group. Especially preferred $R^{19}$ is a group of the formula -(AO)$_w$—$R^{12}$.

In a preferred embodiment, A is an alkylene group having 2 or 3 carbon atoms and especially preferred having 2 carbon atoms. The group -(AO)$_w$— is derived from an alkylene oxide as for example ethylene oxide, propylene oxide, butylene oxide, or any mixture thereof. Especially preferred alkylene oxide is ethylene oxide.

Preferably, the degree of alkoxylation w is from 2 to 20, and more preferably from 4 to 15, as for example from 1 to 20, or from 1 to 15, or from 2 to 25, or from 2 to 15, or from 4 to 25, or from 4 to 20. In a preferred embodiment, the distribution of the alkoxymers is a broad one. In a further preferred embodiment, the distribution of the alkoxymers is a tight one being obtained with a narrow-range catalyst.

In a specific embodiment, the further nonionic surfactant is a fatty acid alkoxylate end-capped with a $C_1$-$C_5$ alkyl group and especially preferred with a methyl group. Such alkoxylates are for example accessible by alkoxylation and especially preferred by ethoxylation of fatty acid methyl esters using an insertion catalyst.

The nonionic surfactants (B) and their methods of preparation are well known to the ones skilled in the art.

A surfactant as defined herein is a compound that will decrease the surface tension when added to the aqueous compositions as described herein. In a comparison of the aqueous composition with and without surfactant, the aqueous composition with surfactant needs to have a lower surface tension.

Additional surfactants for use in the present invention typically contain hydrophobic groups such as alkenyl, cycloalkenyl, alkyl, cycloalkyl, aryl, alkyl/aryl or more complex aryl (as in petroleum sulfonates) moieties being from $C_8$ to $C_{22}$, preferably $C_{10}$ to $C_{20}$, typically $C_{12}$ to $C_{18}$, and a hydrophilic moiety which preferably is a polyethoxy group with 5 to 20 ethoxy units. Other hydrophobic groups included in the invention are polysiloxane groups and polyoxypropylene groups.

The additional surfactant may for example comprise or consist of an at least sparingly water-soluble salt of sulfonic or mono-esterified sulfuric acids, for example an alkylbenzene sulfonate, alkyl sulfate, alkyl ether sulfate, olefin sulfonate, alkane sulfonate, alkylphenol sulfate, alkylphenol ether sulfate, alkylethanolamide sulfate, alkylethanolamide-ether sulfate, or alpha sulfo fatty acid or its ester each having at least one alkyl or alkenyl group with from $C_8$ to $C_{22}$, more usually $C_{10}$ to $C_{20}$, aliphatic atoms.

The expression "ether" here-in-before refers to compounds containing one or more glyceryl groups and/or an oxyalkylene or polyoxyalkylene group especially a group containing from 1 to 150 oxyethylene and/or oxypropylene groups. One or more oxybutylene groups may additionally or alternatively be present. For example, the sulfonated or sulfated surfactant may be sodium dodecyl benzene sulfonate, potassium hexadecyl benzene sulfonate, sodium dodecyl, dimethyl benzene sulfonate, sodium lauryl sulfate, sodium tallow sulfate, potassium oleyl sulfate, ammonium lauryl sulfate, sodium tallow sulfate, potassium oleyl sulfate, ammonium lauryl monoethoxy sulfate, or monoethanolamine cetyl 10 mole ethoxylate sulfate.

Further anionic surfactants which may be added to the current invention include alkyl sulfosuccinates, such as sodium dihexylsulfosuccinate, alkyl ether sulfosuccinates, alkyl sulfosuccinamates, alkyl ether sulfosuccinamates, acylsarcosinates, acyl taurides, isethionates, soaps such as stearates, palmitates, resinates, oleates, linoleates and alkyl ether carboxylates.

Anionic phosphate esters and alkyl phosphonates, alkylamino and imino methylene phosphonates may additionally be used. In each case the further anionic surfactant typically contains at least one alkyl or alkenyl chain having from $C_8$ to $C_{22}$, preferably $C_{10}$ to $C_{20}$. In the case of ethers, there is one or more glyceryl group, and/or from 1 to 150 oxyethylene and/or oxypropylene and/or oxybutylene groups. Preferred anionic surfactants are sodium salts. Other salts of commercial interest include those of potassium, lithium, calcium, magnesium, ammonium, monoethanolamine, diethanolamine, triethanolamine, alkyl amines containing up to seven aliphatic carbon atoms, and alkyl and/or hydroxyl alkyl phosphonium.

The surfactant component of the present invention may further contain or consist of non-ionic surfactants. The non-ionic surfactant may be for example $C_8$ to $C_{22}$ alkanolamides of a mono or di-lower alkanolamine, such as coconut monoethanolamide. Other non-ionic surfactants which may optionally be present, include tertiary acetylenic glycols, polyethoxylated alcohols, polyethoxylated mercaptans, glucamines and their alkoxylates, glucamides and their alkoxylates, alkylpolyglucacides, polyethoxylated carboxylic acids, polyethoxylated amines, polyethoxylated alkylolamides, polyethoxylated alkylphenols, polyethoxylated glyceryl esters, polyethoxylated sorbitan esters, polyethoxylated phosphate esters, and the propoxylate or ethoxylated and propoxylated analogues of all the aforesaid ethoxylated non-ionics, all having a $C_8$ to $C_{22}$ alkyl or alkenyl group and up to 20 ethyleneoxy and/or propyleneoxy groups. Also included are polyoxypropylene/polyethylene oxide block copolymers, polyoxybutylene/polyoxyethylene copolymers and polyoxybuylene/polyoxypropylene copolymers. The polyethoxy, polyoxypropylene and polyoxybutylene compounds may be end capped with, for example benzyl groups to reduce the foaming tendency.

Compositions of the present invention may further contain an amphoteric surfactant. The amphoteric surfactant may for example be a betaine, for example a betaine of the formula $(R^{13})_3N^+CH_2COO^-$, wherein each $R^{13}$ may be the same or different and is an alkyl, cycloalkyl, alkenyl or alkaryl group and preferably at least one, and more preferably not more than one $R^{13}$ has an average of from $C_8$ to $C_{20}$, for example $C_{10}$ to $C_{18}$ of an aliphatic nature and each other $R^{13}$ has an average of from $C_1$ to $C_4$.

Additional amphoteric surfactants for use according to the current invention include quaternary imidazolines, alkyl amine ether sulfates, sulfobetaines and other quaternary amine or quaternised imidazoline sulfonic acids and their salts, and zwitterionic surfactants, for example N-alkyl taurines, carboxylates amidoamines such as $R^{14}CONH(CH_2)_2N''(CH_2CH_2CH_3)_2CH_2CO^-_2$ and amido acids having, in each case, hydrocarbon groups capable of conferring surfactant properties ($R^{14}$ is either alkyl, cycloalkyl alkenyl or alkaryl groups having from $C_8$ to $C_{20}$ of an aliphatic nature). Typical examples include 2-tallow alkyl, 1-tallow amido alkyl, 1-carboxymethyl imidazoline and 2-coconut alkyl N-carboxymethyl 2 (hydroxyalkyl) imidazoline. Generally speaking, any water soluble amphoteric or zwitterionic surfactant compound which comprises a hydrophobic portion including $C_8$ to $C_{20}$ alkyl or alkenyl group and a hydrophilic portion containing an amine or quaternary ammonium group and a carboxylate, sulfate or sulfonic acid group may be used in the present invention.

Compositions of the current invention may further contain other amphoteric surfactant such as an amine oxide, for example an amine oxide containing one or two (preferably one) $C_8$ to $C_{22}$ alkyl group, the remaining substituent or substituents being preferably lower alkyl groups, for example $C_1$ to $C_4$ alkyl groups or benzyl groups. Particularly preferred for use according to the current invention are surfactants which are effective as wetting agents, typically such surfactants are effective at lowering the surface tension between water and a hydrophobic solid surface. Surfactants are preferred which do not stabilize foams to a substantial extent.

Compositions of the present invention may also include additional cationic surfactants. The additional cationic surfactant may for example be a quaternary ammonium compound of the formula (6):

wherein
$R^{18}$ is a $C_5$ to $C_{21}$ aliphatic hydrocarbon group,
X is an anionic counter ion, and
$R^{15}$, $R^{16}$, $R^{17}$ are most typically selected from the group consisting of hydrogen, methyl, ethyl, allyl, propyl, butyl, phenyl or benzyl residues.

Further alkylammonium surfactants for use according to the invention have one or at most two long aliphatic chains per molecule (for example chains having an average of $C_8$ to $C_{20}$ each, usually $C_{12}$ to $C_{18}$ and two or three short chain alkyl groups having $C_1$ to $C_4$ each, for example methyl or ethyl groups, preferably methyl groups. Typical examples include dodecyl trimethyl ammonium salts. Benzalkonium salts having one $C_8$ to $C_{20}$ alkyl group, two $C_1$ to $C_4$ alkyl groups and a benzyl group are also useful. Another useful class of cationic surfactant according to the present invention comprises N-alkyl pyridinium salts wherein the alkyl group has an average of from C to $C_{22}$, preferably $C_{10}$ to $C_{20}$. Other similarly alkylated heterocyclic salts, such as N-alkyl isoquinolinium salts, may also be used. Alkylaryl dialkylammonium salts in which the alkylaryl group is an alkyl benzene group having an average of from $C_8$ to $C_{22}$, preferably $C_{10}$ to $C_{20}$ and the other two alkyl groups usually have from $C_1$ to $C_4$, for example methyl groups are useful. Other classes of cationic surfactant which are of use in the present invention include so called alkyl imidazoline or quaternized imidazoline salts having at least one alkyl group in the molecule with an average of from $C_8$ to $C_{22}$ preferably $C_{10}$ to $C_{20}$. Typical examples include alkyl methyl hydroxyethyl imidazolinium salts, alkyl benzyl hydroxyethyl imidazolinium salts, and 2 alkyl-1-alkylamidoethyl imidazoline salts. Another class of cationic surfactant for use according to the current invention comprises the amido amines such as those formed by reacting a fatty acid having $C_2$ to $C_{22}$ or an ester, glyceride or similar amide forming derivative thereof, with a di or poly amine, such as, for example, ethylene diamine or diethylene triamine, in such a proportion as to leave at least one free amine group. Quaternized amido amines may similarly be employed. Alkyl phosphonium and hydroxyalkyl phosphonium salts having one $C_8$ to $C_{20}$ alkyl group and three $C_1$ to $C_4$ alkyl or hydroxyalkyl groups may also be used as cationic surfactants in the present invention. Typically the additional cationic surfactant may be any water soluble compound having a positively ionized group, usually comprising a nitrogen atom, and either one or two alkyl groups each having an average of from $C_8$ to $C_{22}$. The anionic portion of the cationic surfactant may be any anion which confers water solubility, such as formate, acetate, lactate, tartrate, citrate, chloride, nitrate, sulfate or an alkylsulfate ion having up to $C_4$ such as a higher alkyl sulfate or organic sulfonate. Polyfluorinated anionic, nonionic or cationic surfactants may also be useful in the compositions of the present invention. Examples of such surfactants are polyfluorinated alkyl sulfates and polyfluorinated quaternary ammonium compounds.

Mixtures of two or more of the foregoing surfactants may be used. In particular mixtures of non-ionic surfactants with cationic and/or amphoteric and/or semi polar surfactants or with anionic surfactants may be used. Typically mixtures of anionic and cationic surfactants are avoided, which are often less mutually compatible.

One embodiment uses a further surfactant including at least one N-Aky-N-acylglucamine

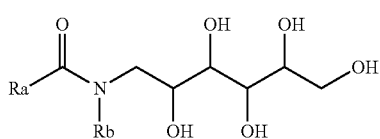

(8)

wherein
Ra is a linear or branched, saturated or unsaturated $C_5$-$C_{21}$-hydrocarbon residue, preferably a $C_7$-$C_{13}$-hydrocarbon residue, and
Rb is a $C_1$-$C_4$ alkyl residue, preferably methyl.

In another preferred embodiment, the N-Alkyl-N-acylglucamines comprise at least 50 wt.-% of the total amount of N-Alkyl-N-acylglucamines (8) compounds with $C_7$-$C_9$-alkyl residue and at least 50 wt.-% of the total amount of N-Alkyl-N-acylglucamines (8) compound with $C_{11}$-$C_{13}$-alkyl residue.

In another embodiment, the surfactant is including at least one cyclic N-Aky-N-acylglucamine of the following formula

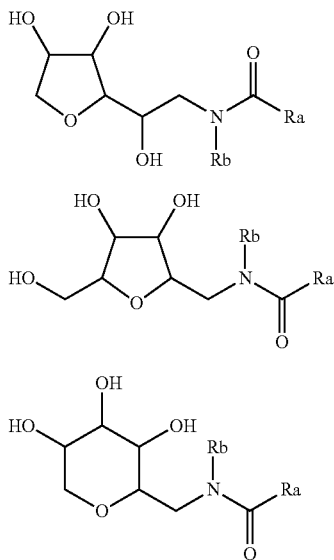

(9)

(10)

(11)

whereas in formula (9), (10) and (11)
Ra is a linear or branched, saturated or unsaturated $C_5$-$C_{21}$-alkyl residue, preferably a $C_7$-$C_{13}$-alkyl residue, and
Rb is a $C_1$-$C_4$-alkyl residue, preferably methyl.

The concentration of components A) and B) of the inventive embodiments of the composition will provide a synergistic improvement of the performance of component A) alone. The ratio between the components A) and B) may vary in the range of 5 wt % to 95 wt % and 95 wt % to 5 wt %. In a preferred embodiment, the concentration is in the range of 15 wt % to 85 wt % A) and 85 wt % to 15 wt % B). In another preferred embodiment, the weight ratio between A) and B) is A):B)=33 wt % to 66 wt %.

Whether or not there is a synergy between components A) and B) is determined by the reduced dose rate to prevent gas hydrate agglomeration over the dose rate required of each of the individual components.

In a second aspect, the instant invention provides a method for inhibiting gas hydrate formation, the method comprising bringing a system containing hydrocarbons and water susceptible to gas hydrate formation in contact with the composition according to the first aspect.

In a third aspect, the instant invention provides the use of the composition according to the first aspect for inhibiting gas hydrate formation in a system containing hydrocarbons and water.

In a fourth aspect, the instant invention provides improved water drop properties, including a reduction of the time to achieve significant water drop and a reduction of the absolute amount of water remaining emulsified into the co-produced oil.

Preferably, R1 is an alkyl group having 3-4 carbon atoms and most preferred when R1 is an alkyl group having 4 carbon atoms;
Preferably, R2 is an alkyl group having 3-4 carbon atoms and most preferred when R1 is an alkyl group having 4 carbon atoms;
Preferably, R3 when present is hydrogen or organic moieties having from 1 to 16 carbon atoms and most preferred when R3 is hydrogen;
Preferably, R4 is —$(CH_2)_t$— or —$[CH_2$—$CHR_6)_t]$— and most preferred when R4 is —$(CH_2)_t$—;
Preferably, R5 is an alkyl or alkenyl group having 8 to 22 carbon atoms and most preferred when R5 is an alkyl or alkenyl group having 8 to 18 carbon atoms;
Preferably, R6 is hydrogen or an alkyl group having from 1 to 4 carbon atoms and most preferred when R6 is hydrogen;
Preferably, R7 is hydrogen or an alkyl group having from 1 to 4 carbon atoms and most preferred when R7 is hydrogen;
Preferably, R8 when present is hydrogen or an alkyl group having from 1 to 4 carbon atoms and most preferred when R8 is hydrogen;
Preferably, n is 0 or 1 and most preferred when n=0
Preferably, m is 0 or 2 and most preferred when m=0
Preferably, o is 0 or 2 and most preferred when o=0
Preferably, p is 0 or 1 and most preferred when p=1
Preferably, t is 2, 3 or 4 and most preferred when t=3;
$X^-$ is preferably selected from hydroxide, carboxylate, halide, sulfate, organic sulfonate, acrylate, methacrylate, and combinations thereof. Suitable halide ions include, without limitation, bromide, chloride, and combinations thereof; $X^-$ is more preferably selected from carboxylate, halide, acrylate, methacrylate, and combinations thereof; and is most preferred when $X^-$ is acrylate.

In one preferred embodiment, R3 is hydrogen, and the anion $X^-$ is selected from hydroxide, carboxylate, halide, sulfate, organic sulfonate, and combinations thereof.

In a still further embodiment, the compound according to formula (1) is the reaction product of an N,N-dialkylaminoalkylamine with a fatty acid, a fatty acid ester or glyceride. Preferably, the fatty acid, ester or glyceride is derived from a plant source or an animal source, selected from coconut oil, tallow oil, vegetable oil, and combinations thereof.

In another embodiment, the compound according to formula (1) includes a product prepared by the reaction of an amine selected from (3-dialkylamino)propylamine and (3-dialkylamino)ethylamine with vegetable oil or tallow oil followed by reacting with a reactant selected from an organic halide, such as an alkyl halide, having from 4 to 20 carbon atoms, hydrogen peroxide, and an acid, wherein the acid is selected from mineral acids, formic acid, acetic acid, chloroacetic acid, propionic acid, acrylic acid, and methacrylic acid, and wherein the dialkyl of the (3-dialkylamino) propylamine includes two alkyl groups independently selected from methyl, ethyl, propyl, butyl, morpholine, piperidine, and combinations thereof.

This invention relates to a method and a composition used therein for inhibiting, retarding, mitigating, reducing, controlling and/or delaying formation of hydrocarbon hydrates or agglomerates of hydrates. The method may be applied to prevent or reduce or mitigate plugging of conduits, pipes, transfer lines, valves, and other places or equipment where hydrocarbon hydrate solids may form under the conditions.

The term "inhibiting" is used herein in a broad and general sense to mean any improvement in preventing, controlling, delaying, reducing or mitigating the formation, growth and/or agglomeration of hydrocarbon hydrates, particularly light hydrocarbon gas hydrates in any manner, including, but not limited to kinetically, thermodynamically, by dissolution, by breaking up, other mechanisms, or any combinations thereof.

The term "formation" or "forming" relating to hydrates is used herein in a broad and general manner to include, but are not limited to, any formation of hydrate solids from water and hydrocarbon(s) or hydrocarbon gas(es), growth of hydrocarbon hydrate solids, agglomeration of hydrocarbon hydrates, accumulation of hydrocarbon hydrates on surfaces, any deterioration of hydrate solids plugging or other problems in a system and combinations thereof.

The present method is useful for inhibiting hydrate formation for many hydrocarbons and hydrocarbon mixtures. The method is particularly useful for lighter or low-boiling, $C_1$-$C_5$, hydrocarbon gases or gas mixtures at ambient conditions. Non-limiting examples of such "low-boiling" gases include methane, ethane, propane, n-butane, isobutane, iso-pentane and mixtures thereof. Other examples include various natural gas mixtures that are present in many gas and/or oil formations and natural gas liquids (NGL). The hydrates of all of these low-boiling hydrocarbons are also referred to as gas hydrates. The hydrocarbons may also comprise other compounds including, but not limited to $CO_2$, hydrogen sulfide, and other compounds commonly found in gas/oil formations or processing plants, either naturally occurring or used in recovering/processing hydrocarbons from the formation or both, and mixtures thereof.

The method of the present invention involves contacting a hydrocarbon and water mixture with a suitable compound or composition. When an effective amount of the compound is used, hydrate blockage is prevented or at least delayed. In the absence of such effective amount, hydrate blockage is not prevented nor delayed.

The contacting may be achieved by a number of ways, including mixing, blending with mechanical mixing equipment or devices, stationary mixing setup or equipment, magnetic mixing or other suitable methods, other equipment and means known to one skilled in the art and combinations thereof to provide adequate contact and/or dispersion of the composition in the mixture. The contacting can be made in-line or offline or both. The various components of the composition may be mixed prior to or during contact, or both. As discussed, if needed or desired, the composition or some of its components may be optionally removed or separated mechanically, chemically, or by other methods known to one skilled in the art, or by a combination of these methods after the hydrate formation conditions are no longer present.

Because the present invention is particularly suitable for lower boiling hydrocarbons or hydrocarbon gases at ambient conditions, the pressure of the condition is usually at or greater than atmospheric pressure. (i.e. about 101 kPa), preferably greater than about 1 MPa, and more preferably greater than about 5 MPa. The pressure in certain formation or processing plants or units could be much higher, say greater than about 20 MPa. There is no specific high-pressure limit. The present method can be used at any pressure that allows formation of hydrocarbon gas hydrates.

The temperature of the condition for contacting is usually below, the same as, or not much higher than the ambient or room temperature. Lower temperatures tend to favor hydrate formation, thus requiring the treatment with the composition of the present invention. At much higher temperatures, however, hydrocarbon hydrates are less likely to form, thus obviating the need of carrying out any treatments.

The composition may also include solvent. These are generally solvents for the virgin solid form of the compounds. Such solvents include, but are not limited to, water, simple alcohols like methanol, ethanol, iso-propanol, n-butanol, iso-butanol, 2-ethyl hexanol; glycols like ethylene glycol, 1,2-propylene glycols, 1,3-propylene glycol, and hexylene glycol; ether solvents like ethylene glycol mono butylether (butyl cellosolve), ethylene glycol dibutyl ether, and tetrahydrofuran; ketonic solvents like methylethylketone, diisobutylketone, N-methylpyrrolidone, cyclohexanone; armatic hydrocarbon solvents like xylene and toluene; and mixtures thereof. The selection of the suitable solvent or combination of solvents are important to maintain a stable solution of the compounds during storage and to provide stability and reduced viscosity for the inhibitor solutions when they are injected against a pressure of 200 to 25,000 psi. The solvent preferably is present in the inhibitor composition in the range from 0% to about 95%, preferably from 20% to about 95%, more preferably from 50% to about 95% of the total composition, based on volume.

The compounds of the present invention are added into the mixture of hydrocarbons and water at any concentration effective to inhibit the formation of hydrates under the given conditions. Preferably, the concentration of the active gas hydrate inhibitor composition is between about 0.01 wt.-% and about 5 wt.-% based on the water content. More preferably, the gas hydrate inhibitor composition concentration is between about 0.1 wt.-% and about 3 wt.-%.

The present invention may also be used in combination with other means of hydrate inhibition such as the use of thermodynamic or kinetic inhibitors discussed in the background section. These other hydrate inhibitors may be of the same or different type of hydrate inhibitor used in the composition. If mixtures of hydrate inhibitors are used, the mixture may be added to the hydrocarbon and water containing process stream through a single port or multiple ports. Alternatively, individual hydrate inhibitors may be added at separate ports to the process stream.

The present invention may also be used in combination with other oil field flow assurance and integrity compounds such as, but not limited to, corrosion inhibitors, scale inhibitors, paraffin inhibitors, asphaltene inhibitors, drilling fluids, fracturing fluids, completion fluids, antifoams, emulsion breakers, and/water clarifiers.

EXAMPLES

Test Procedure 1: Evaluation of Hydrate Inhibitor Compounds in Parallel Process Development Reactors To a 100 mL stainless steel reactor, attached to thermostat and a liquid handling system, dodecane (10 mL), brine (20 mL of 5% NaCl, density of 1.07 g/cm$^3$ at 25° C.), and the anti-agglomerant formulation were added at 30° C. The reactor was pressurized to 95 bar with Erdgas H (see Table 1 for composition). The stirrer speed was adjusted to 1000 rpm for 1 min to saturate the liquid with gas. Subsequently the stirrer speed was reduced to 200 rpm, and a temperature setting of −10° C. was initiated. Monitoring the internal temperature of the reactor showed a characteristic exotherm indicative of hydrate formation below a threshold temperature. If the exotherm was accompanied by a prolonged increase in stirrer power uptake this was indicative of agglomeration, signifying a failure. If the stirrer power remained constant or following an increase returned to the original baseline, agglomeration was prevented; indicating a pass.

For evaluation of their hydrate inhibitor performance, the testing was started with 0.3 wt.-% of the hydrate inhibitor, formulated as a 60% active solution in methanol. If samples failed at this dose rate, they were labelled as >0.3 wt.-% minimum effective dose (MED) and were not tested further. If samples initially tested at 0.3 wt.-% passed, they were sequentially and incrementally reduced in dose rate by 0.05 wt.-% each time until a dose rate was used that failed. When that occurred, the last passing dose rate was input into the Table (4) as the Minimum Effective Dose (MED).

TABLE 1

Erdgas H gas composition

| Component Name | Chemical Symbol | Amount (mol-%) |
|---|---|---|
| Nitrogen | $N_2$ | 0.14 |
| Carbon Dioxide | $CO_2$ | 0 |
| Methane | $C_1$ | 87.56 |
| Ethane | $C_2$ | 7.6 |
| Propane | $C_3$ | 3 |
| i-Butane | i-$C_4$ | 0.5 |
| n-Butane | n-$C_4$ | 0.8 |
| i-Pentane | i-$C_5$ | 0.2 |
| n-Pentane | n-$C_5$ | 0.2 |

Monitoring of the internal temperature of the reactor shows a characteristic exotherm indicative of hydrate formation below a threshold temperature. If the exotherm is accompanied by a prolonged increase in stirrer power uptake this is indicative of agglomeration; signifying a failure. If the stirrer power remains constant or following an increase returns to the original baseline, agglomeration is prevented; indicating a pass.

Water Drop Testing

When appraising Anti-Agglomerants, performance is obviously the highest criteria to consider, however there are several secondary properties that should also be considered that can have an effect on the operational system to which the AA's are applied. It should be realized that both the primary criteria of performance as well as the secondary properties needs to be met for a particular chemistry or product to be suitable for use within an operational system. The water drop of the embodiments here (actives plus synergists), were surprisingly better relative to the standard AA's alone. When considering the water drop, a time period was chosen that would be considered aggressive (less time) for offshore separation, in part to ensure good translation to eventual field application conditions. Specifically, at the total water drop (amount of expected water to be separated) was observed after vigorous mixing (created emulsion), with a time duration of 1 minute.

Experimental Details:

Into a graduated 100 mL cylinder with conical bottom (typically used for emulsion testing), 50 mL of oil and 50 mL of water were charged. The water was 6% brine (using NaCl) and the oil was a medium crude from the Gulf of Mexico. To the 100 mL of total fluids 1 wt.-% in respect to the aqueous phase of a hydrate inhibitor (as a 60 wt.-% active formulation) were added. A dose rate of 1% was deliberately chosen to highlight the effect of the hydrate inhibitors on the water drop. The bottles were capped, shaken vigorously by hand, and allowed to stand at room temperature for 1 minute, at which point the amount of water that could be observed as a separate phase was recorded. This number was then multiplied by 2 to obtain the results shown in Table 4 as a percent of water present. A value of 100% means that all the water was observed as a separate phase. If less than 100% was observed, the remaining water was either within the oil or as part of a "rag layer" or emulsion layer.

For testing, gas hydrate inhibitor formulations were prepared by blending amphiphiles (A) according to table 2 and cationic surfactants (B) according to table 3 with the weight ratios according to table 4. For ease of handling, the formulations were adjusted to 60 wt.-% active content with methanol.

These formulations were tested for their minimum dosage rate for hydrate inhibition according to test procedure 1. The minimum dosage rates for a pass given in table 4 refer to the required minimum dosage of active ingredient.

TABLE 2

Characterization of tested gas hydrate inhibitors A) according to Formula 1 wherein:

| Residue | A1 | A2 |
|---|---|---|
| $R^1$ | n-butyl | n-butyl |
| $R^2$ | n-butyl | n-butyl |
| $R^3$ | $C_2H_5$ | H |
| $R^4$ | —$(CH_2)_t$— | —$(CH_2)_t$— |
| $R^5$ | $C_{12}H_{25}$ | Coco alkyl |
| $R^6$ | H | H |
| $R^7$ | H | — |
| $R^8$ | — | — |
| m | 0 | 0 |
| n | 1 | 0 |
| o | 2 | 0 |
| p | 1 | 1 |
| t | 3 | 3 |
| u | — | — |
| $X^-$ | ethyl sulfate | acrylate |

TABLE 3

Characterization of tested nonionic surfactants B)

| | |
|---|---|
| B1 | Coconut fatty amine ethoxylate with 5 EO |
| B2 | Coconut fatty alcohol ethoxylate with 5 EO, butyl end-capped |

TABLE 3-continued

Characterization of tested nonionic surfactants B)

| | |
|---|---|
| B3 | $C_{12}$-$C_{18}$ fatty alcohol ethoxylate with 10 EO |
| B4 | $C_{12}$/$C_{15}$-oxo alcohol with 5 PO and 2 EO |
| B5 | Isodecanol ethoxylate with 3 EO |
| B6 | $C_{12}$-$C_{14}$ alcohol ethoxylate with 7 EO |
| B7 | Oleyl alcohol ethoxylate with 8 EO |
| B8 | Tallow fatty alcohol ethoxylate with 20 EO; the alcohol containing as main components 24% palmitic acid and 62% stearic acid |
| B9 | Isotridecanol ethoxylate with 6 EO |
| B10 | Isotridecanol ethoxylate with 8 EO, methyl end-capped |
| B11 | Coco fatty acid ethoxylate with 4 EO |
| B12 | Palm fatty acid ethoxylate with 6 EO, methyl end-capped; with narrow-range distribution of ethoxylates; the palm fatty acid containing as main components 43-% palmitic acid; 5% stearic acid; 40% oleic acid; and 9% of linoleic acid |
| B13 (comp.) | Sorbitan monolaurate |
| B14 (comp.) | Cardanol ethoxylate with 8 EO |

Coco alkyl comprises as main components 51 wt.-% $C_{12}H_{25}$, and 16 wt.-% $C_{14}H_{29}$. All percentages given in table 3 refer to percent per weight.

TABLE 4

| | Gas hydrate inhibitor (wt.-% active) | | MED | water drop |
|---|---|---|---|---|
| Example | Amphiphile A | Surfactant B | (wt.-%) | (%) |
| Results from autoclave testing (components testing; comparative) | | | | |
| 1 (comp.) | A1 (100) | — | 0.30 | 80 |
| 2 (comp.) | A2 (100) | — | 0.30 | 84 |
| 5 (comp.) | — | B1 (100) | >0.30[a] | 62 |
| 6 (comp.) | — | B2 (100) | >0.30[a] | 64 |
| 7 (comp.) | — | B3 (100) | >0.30[a] | 62 |
| 8 (comp.) | — | B4 (100) | >0.30[a] | 66 |
| 9 (comp.) | — | B5 (100) | >0.30[a] | 58 |
| 10 (comp.) | — | B6 (100) | >0.30[a] | 64 |
| 11 (comp.) | — | B7 (100) | >0.30[a] | 62 |
| 14 (comp.) | — | B8 (100) | >0.30[a] | 70 |
| 15 (comp.) | — | B9 (100) | >0.30[a] | 66 |
| 17 (comp.) | — | B10 (100) | >0.30[a] | 64 |
| 18 (comp.) | — | B11 (100) | >0.30[a] | 68 |
| 19 (comp.) | — | B12 (100) | >0.30[a] | 64 |
| 20 (comp.) | — | B13 (100) | 0.30 | 60 |
| 21 (comp.) | — | B14 (100) | >0.30[a] | 60 |
| Results from autoclave testing (formulations containing A1) | | | | |
| 22 | A1 (50.0) | B1 (50.0) | 0.10 | 86 |
| 23 | A1 (71.4) | B1 (28.6) | 0.10 | 88 |
| 24 | A1 (50.0) | B2 (50.0) | 0.15 | 90 |
| 25 | A1 (71.4) | B2 (28.6) | 0.10 | 88 |
| 26 | A1 (50.0) | B3 (50.0) | 0.10 | 90 |
| 27 | A1 (71.4) | B3 (28.6) | 0.10 | 92 |
| 28 | A1 (50.0) | B4 (50.0) | 0.15 | 90 |
| 29 | A1 (71.4) | B4 (28.6) | 0.10 | 90 |
| 30 | A1 (50.0) | B5 (50.0) | 0.15 | 88 |
| 31 | A1 (71.4) | B5 (28.6) | 0.15 | 90 |
| 32 | A1 (50.0) | B6 (50.0) | 0.10 | 92 |
| 33 | A1 (71.4) | B6 (28.6) | 0.10 | 94 |
| 34 | A1 (28.6) | B6 (71.4) | 0.15 | 90 |
| 35 | A1 (50.0) | B7 (50.0) | 0.20 | 88 |
| 36 | A1 (71.4) | B7 (28.6) | 0.15 | 90 |
| 37 | A1 (50.0) | B8 (50.0) | 0.20 | 92 |
| 38 | A1 (71.4) | B8 (28.6) | 0.20 | 94 |
| 39 (comp.) | A1 (50.0) | B13 (50.0) | 0.25 | 82 |
| 40 (comp.) | A1 (71.4) | B13 (28.6) | 0.30 | 80 |
| 41 (comp.) | A1 (50.0) | B14 (50.0) | >0.30[a] | 82 |
| 42 (comp.) | A1 (71.4) | B14 (28.6) | 0.30 | 82 |
| Results from autoclave testing (formulations containing A2) | | | | |
| 43 | A2 (50.0) | B1 (50.0) | 0.10 | 92 |
| 44 | A2 (71.4) | B1 (28.6) | 0.05 | 94 |
| 45 | A2 (50.0) | B2 (50.0) | 0.10 | 94 |
| 46 | A2 (71.4) | B2 (28.6) | 0.10 | 94 |
| 47 | A2 (50.0) | B3 (50.0) | 0.10 | 96 |

TABLE 4-continued

| | Gas hydrate inhibitor (wt.-% active) | | MED | water drop |
|---|---|---|---|---|
| Example | Amphiphile A | Surfactant B | (wt.-%) | (%) |
| 48 | A2 (71.4) | B3 (28.6) | 0.05 | 94 |
| 49 | A2 (50.0) | B4 (50.0) | 0.15 | 96 |
| 50 | A2 (71.4) | B4 (28.6) | 0.15 | 96 |
| 51 | A2 (50.0) | B6 (50.0) | 0.10 | 96 |
| 52 | A2 (71.4) | B6 (28.6) | 0.10 | 98 |
| 54 | A2 (50.0) | B7 (50.0) | 0.20 | 94 |
| 55 | A2 (71.4) | B7 (28.6) | 0.20 | 94 |
| 56 | A2 (50.0) | B9 (50.0) | 0.15 | 92 |
| 57 | A2 (71.4) | B9 (28.6) | 0.15 | 94 |
| 58 | A2 (50.0) | B10 (50.0) | 0.10 | 94 |
| 59 | A2 (71.4) | B10 (28.6) | 0.10 | 94 |
| 60 | A2 (50.0) | B11 (50.0) | 0.10 | 96 |
| 61 | A2 (71.4) | B11 (28.6) | 0.05 | 98 |
| 62 | A2 (50.0) | B12 (50.0) | 0.10 | 94 |
| 663 | A2 (71.4) | B12 (28.6) | 0.10 | 92 |
| 64 (comp.) | A2 (50.0) | B13 (50.0) | 0.30 | 90 |
| 65 (comp.) | A2 (71.4) | B13 (28.6) | 0.25 | 88 |
| 66 (comp.) | A2 (50.0) | B14 (50.0) | >0.30[a] | 86 |
| 67 (comp.) | A2 (71.4) | B14 (28.6) | 0.30 | 84 |

[a] >0.30 wt.-% means it did not pass at 0.30 wt.-% dose rate and was not tested at higher concentration.

The invention claimed is:

1. A method for inhibiting gas hydrate formation in a system containing hydrocarbons and water, comprising the step of contacting the system with a gas hydrate inhibitor composition comprising (A) a compound according to formula (1)

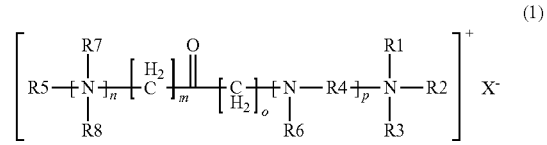

wherein
R1 is an alkyl group having from 1 to 5 carbon atoms;
R2 is hydrogen or an alkyl group having from 1 to 5 carbon atoms;
R3 is present or not as hydrogen and organic moieties having from 1 to 20 carbon atoms;
R4 is selected from —(CH2)t—, —[(CH2—CHR6)t]—, —(CH2—CHR6O)u—(CH2)t— and combinations thereof;
R5 is an alkyl or alkenyl group having 4 to 22 carbon atoms;
R6 is hydrogen or an alkyl group having from 1 to 4 carbon atoms;
R7 is hydrogen or an alkyl group having from 1 to 4 carbon atoms;
R8 is present or not as hydrogen or organic moieties having from 1 to 20 carbon atoms;
t is 2, 3 or 4;
u is an integer between 0 and 100;
n is 0 or 1
m is 0 or 2
o is 0 or 2
p is 0 or 1
$X^-$ is an anion,
and
(B) a compound that is a synergistic surfactant which is selected from the group consisting of alkoxylated $C_8$-$C_{18}$ fatty alcohols, alkoxylated $C_8$-$C_{18}$ fatty amines, alkoxylated $C_8$-$C_{18}$ fatty acids and alkoxylated $C_8$-$C_{18}$ fatty acid amides,
wherein (A) and (B) are present in a weight ratio (A):(B) of from 15:85 to 85:15.

2. The method for inhibiting gas hydrate formation in a system containing hydrocarbons and water according to claim 1, wherein
(B) is an alkoxylated $C_8$-$C_{18}$ fatty alcohol, an alkoxylated $C_8$-$C_{18}$ fatty amine, an alkoxylated $C_8$-$C_{18}$ fatty acid, and/or an alkoxylated $C_8$-$C_{18}$ fatty acid amide of general formula (19):

$$R^{11}\text{—Y-}(AO)_w\text{—}R^{12} \quad (19)$$

wherein
$R^{11}$ is an alkyl or alkenyl group having 8 to 18 carbon atoms;
Y is —O—, —N($R^{19}$)—, —C(=O)—O— or —C(=O)—N($R^{19}$)—;
A is a $C_1$ to $C_4$ alkylene group;
$R^{12}$ is hydrogen, an alkyl group having from 1 to 5 carbon atoms, a benzyl group, or —C(O)—$R^{20}$;
$R^{19}$ is hydrogen, an alkyl group having from 1 to 18 carbon atoms, an alkenyl group having 3 to 18 carbon atoms, or a group of formula -(AO)$_w$—$R^{12}$;
$R^{20}$ is a $C_1$ to $C_5$-hydrocarbyl group; and
w is an integer between 1 and 25.

3. The method for inhibiting gas hydrate formation in a system containing hydrocarbons and water according to claim 1, wherein $X^-$ is selected from the group consisting of hydroxide, carboxylate, halide, sulphate, organic sulphonate, acrylate, methacrylate, and combinations thereof.

4. The method for inhibiting gas hydrate formation in a system containing hydrocarbons and water according to claim 1, wherein B is selected from the group consisting of coconut fatty amine ethoxylates with 5 EO, $C_{12}$-$C_{18}$ fatty alcohol ethoxylates with 10 EO, and $C_{12}$-$C_{14}$ alcohol ethoxylates with 7 EO.

5. The method for inhibiting gas hydrate formation in a system containing hydrocarbons and water according to claim 1, wherein R3 is hydrogen, and the anion $X^-$ is selected from the group consisting of hydroxide, carboxylate, halide, sulphate, organic sulphonate, and combinations thereof.

6. The method for inhibiting gas hydrate formation in a system containing hydrocarbons and water according to claim 1, wherein the step of contacting may be achieved by mixing, blending with mechanical mixing equipment or devices, stationary mixing setup or equipment, magnetic mixing or combinations thereof to provide contact or dispersion of the gas hydrate inhibitor composition in the mixture.

7. The method for inhibiting gas hydrate formation in a system containing hydrocarbons and water according to claim 1, wherein the step of contacting can be made in-line or offline or both.

8. The method for inhibiting gas hydrate formation in a system containing hydrocarbons and water according to claim 1, wherein the pressure is at or greater than atmospheric pressure.

9. The method for inhibiting gas hydrate formation in a system containing hydrocarbons and water according to claim 1, wherein the pressure is greater than about 1 MPa.

10. The method for inhibiting gas hydrate formation in a system containing hydrocarbons and water according to claim 1, wherein the gas hydrate inhibitor composition further comprises at least one solvent.

11. The method for inhibiting gas hydrate formation in a system containing hydrocarbons and water according to claim 10, wherein the solvent is selected from the group consisting of water, methanol, ethanol, iso-propanol, n-butanol, iso-butanol, 2-ethyl hexanol, ethylene glycol, 1,2-propylene glycols, 1,3-propylene glycol, hexylene glycol, ethylene glycol mono butylether (butyl cellosolve), ethylene glycol dibutyl ether, tetrahydrofuran, methylethylketone, diisobutylketone, N-methylpyrrolidone, cyclohexanone, xylene, toluene, and mixtures thereof.

12. The method for inhibiting gas hydrate formation in a system containing hydrocarbons and water according to claim 10, wherein the solvent is present in the gas hydrate inhibitor composition in the range from 0.1% to about 95%, based on the volume of the gas hydrate inhibitor composition.

13. The method for inhibiting gas hydrate formation in a system containing hydrocarbons and water according to claim 1, wherein the system containing hydrocarbons and water is contacted with an amount of the gas hydrate inhibitor composition that is between about 0.01 wt.-% and about 5 wt.-% of the weight of water in the system containing hydrocarbons and water.

14. The method for inhibiting gas hydrate formation in a system containing hydrocarbons and water according to claim 1, wherein the gas hydrate inhibitor composition further comprises thermodynamic or kinetic gas hydrate inhibitors.

15. The method for inhibiting gas hydrate formation in a system containing hydrocarbons and water according to claim 1, wherein
$R^1$ is n-butyl,
$R^2$ is n-butyl,
$R^3$ is $C_2H_5$,
$R^4$ is —(CH$_2$)$_t$—,
$R^5$ is $C_{12}H_{25}$,
$R^6$ is H,
$R^7$ is H,
$R^8$ is not present,
m is 0,
n is 1,
o is 2,
p is 1,
t is 3,
u is not present, and
$X^-$ is ethyl sulfate.

16. The method for inhibiting gas hydrate formation in a system containing hydrocarbons and water according to claim 1, wherein
$R^1$ is n-butyl,
$R^2$ is n-butyl,
$R^3$ is H,
$R^4$ is —(CH2)t—,
$R^5$ is coco alkyl,
$R^6$ is H,
$R^7$ is not present,
$R^8$ is not present,
m is 0,
n is 0,
o is 0,
p is 1,
t is 3,
u is not present, and
$X^-$ is acrylate.

17. A method for inhibiting gas hydrate formation in a system containing hydrocarbons and water, comprising the step of contacting the system with a gas hydrate inhibitor composition comprising (A) a compound according to formula (1a)

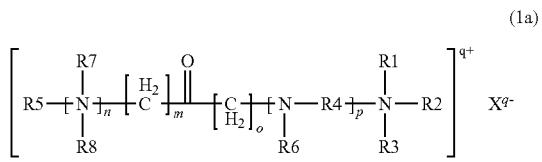

(1a)

wherein

R1 is an alkyl group having from 1 to 5 carbon atoms;
R2 is hydrogen or an alkyl group having from 1 to 5 carbon atoms;
R3 is present or not as hydrogen and organic moieties having from 1 to 20 carbon atoms;
R4 is selected from —$(CH_2)_t$—, —$[CH_2$—$CHR^6)_t]$—, —$(CH_2$—$CHR^6O)_u$—$(CH_2)_t$— and combinations thereof;
R5 is an alkyl or alkenyl group having 4 to 22 carbon atoms;
R6 is hydrogen or an alkyl group having from 1 to 4 carbon atoms;
R7 is hydrogen or an alkyl group having from 1 to 4 carbon atoms;
R8 is present or not as hydrogen or organic moieties having from 1 to 20 carbon atoms;
t is 2, 3 or 4;
u is an integer between 0 and 100;
n is 0 or 1
m is 0 or 2
o is 0 or 2,
p is 0 or 1,
q is an integer between 0 and 2
$X^-$ is an anion,
wherein q is 0 when R3 and R8 are absent; q is 1 when one of R3 and R8 is present and the other is absent; and q is 2 when R3 and R8 are both present
and
(B) a compound that is a synergistic surfactant which is selected from the group consisting of alkoxylated $C_8$-$C_{18}$ fatty alcohols, alkoxylated $C_8$-$C_{18}$ fatty amines, alkoxylated $C_8$-$C_{18}$ fatty acids and alkoxylated $C_8$-$C_{18}$ fatty acid amides;
wherein (A) and (B) are present in a weight ratio (A):(B) of from 15:85 to 85:15.

18. The method for inhibiting gas hydrate formation in a system containing hydrocarbons and water according to claim 1, wherein
$R^1$ is n-butyl,
$R^2$ is n-butyl,
$R^3$ is $C_2H_5$ or H,
$R^4$ is —$(CH_2)t$—,
$R^5$ is $C_{12}H_{25}$ or coco alkyl,
$R^6$ is H,
$R^7$ if present, is H
$R^8$ is not present,
m is 0,
n is 0 or 1,
o is 0 or 2,
p is 1,
t is 3,
u is not present, and
$X^-$ is ethyl sulfate or acrylate.

19. The method for inhibiting gas hydrate formation in a system containing hydrocarbons and water according to claim 1, wherein the gas hydrate inhibitor composition comprises an amount of (A) that is at least 50 wt % of the total weight of (A) and (B) in the gas hydrate inhibitor composition.

* * * * *